United States Patent [19]

Jouffret

[11] 3,948,995

[45] Apr. 6, 1976

[54] PROCESS FOR CONVERTING ALKYLAROMATIC HYDROPEROXIDES INTO PHENOLIC PRODUCTS AND CARBONYL PRODUCTS

[75] Inventor: Michel Jouffret, Francheville-le-Bas (Rhone), France

[73] Assignee: Rhone-Poulenc-Textile, Paris, France

[22] Filed: July 24, 1974

[21] Appl. No.: 491,486

[30] Foreign Application Priority Data

July 27, 1973 France .............................. 73.27647

[52] U.S. Cl. .......... 260/592; 260/586 P; 260/593 A; 260/599; 260/601 R; 260/621 C; 260/622 R; 260/623 R; 260/624 R; 260/590 R; 260/600 R
[51] Int. Cl.$^2$ .................. C07C 45/00; C07C 37/08
[58] Field of Search ........ 260/593 A, 621 C, 610 R, 260/592, 599, 601, 590 R, 591, 600, 622 R, 623 R, 624 R

[56] References Cited
UNITED STATES PATENTS

| | | | |
|---|---|---|---|
| 2,853,532 | 9/1958 | De Jong | 260/593 |
| 3,497,561 | 2/1970 | Gelbein | 260/593 |

OTHER PUBLICATIONS

Stannett et al., J.A.C.S., Vol. 72, pp. 4125–4130 (1950).

Primary Examiner—James O. Thomas, Jr.
Assistant Examiner—James H. Reamer
Attorney, Agent, or Firm—Cushman, Darby & Cushman

[57] ABSTRACT

A process for splitting primary or secondary alkylaromatic hydroperoxides into phenolic products and carbonyl products is disclosed which consists of reacting the hydroperoxide with a catalytic amount of an acid in the presence of an aprotic polar solvent which is a polymethylene-sulphone or an alkylene glycol carbonate which contains 2 to 4 carbon atoms (in the alkylene part).

11 Claims, No Drawings

PROCESS FOR CONVERTING ALKYLAROMATIC HYDROPEROXIDES INTO PHENOLIC PRODUCTS AND CARBONYL PRODUCTS

The present invention relates to a process for splitting alkylaromatic hydroperoxides, by means of compounds with an acid reaction, into phenolic products and carbonyl products.

It is known that simple as well as substituted phenols and carbonyl products, both aldehydes and ketones, can be prepared simultaneously by the decomposition, preferably by means of acidic substances, of hydroperoxides of alkylaromatic hydrocarbons, these hydroperoxides being primary, secondary or tertiary. The splitting reaction is generally carried out in the presence of an organic solvent which is inert towards the reactants; examples of such solvents are aliphatic, cycloaliphatic and aromatic hydrocarbons, alcohols, phenols, ketones, esters, ethers and liquid chlorinated hydrocarbons.

Although tertiary alkylaromatic hydroperoxides give rise readily under these conditions to phenols and ketones with industrially valuable yields, it has been found, in contrast, that primary and secondary alkylaromatic hydroperoxides decompose less readily to form phenols and aldehydes, and the processes which have been described generally possess disadvantages which have limited their industrial usefulness.

Amongst the prior art processes, some involve carrying out the reaction in the presence of liquid aromatic hydrocarbons, for example those from which they are derived by oxidation, using aqueous sulphuric acid; the crude oxidised products containing the hydroperoxides are thus advantageously used for the reaction. It has been found that the amount (expressed as pure acid) of the aquoues solutions of sulphuric acid used for the splitting process can be as high as or greater than that of the hydroperoxide employed, the concentration of acid being generally from 20% to 65% by weight. In the majority of these processes, the reaction mixture thus consists of two non-miscible phases, one aqueous and the other organic, and, as a result, vigorous and prolonged stirring is necessary in order to establish contact between the molecules of hydroperoxide and those of the acid, which is desirable in order that the reaction shall take place satisfactorily. Moreover, an additional step of isolating the aqueous phase is required. For these reasons such processes are not of great industrial value.

It has also been proposed to carry out the splitting reaction in an anhydrous or practically anhydrous medium, using a catalytic amount of a concentrated strong acid, for example concentrated sulphuric acid, in the presence of a suitable organic solvent such as methanol (see, for example, French Pat. No. 1,054,032). Such a process certainly makes it possible to work in a homogeneous medium and is free from the disadvantages mentioned above for the processes using aqueous sulphuric acid and a hydrocarbon solvent. However, the sulphuric acid/methanol combination is less active than aqueous sulphuric acid and requires longer reaction times in order to achieve high degrees of conversion of the hydroperoxide. Its use consequently involves a decrease in the productivity of the equipment; thus the reaction involving the splitting of p-xylyl hydroperoxide with concentrated sulphuric acid in methanol, using 2.69% by weight of acid relative to the hydroperoxide, requires a minimum time of 2½ hours, giving p-cresol in a yield, relative to the hydroperoxide employed, which does not exceed 44%.

In short, the various proposals in the prior art for carrying out the splitting of primary and secondary alkylaromatic hydroperoxides into phenolic products and aldehyde products, on an industrial scale, are not completely satisfactory. The present invention aims to resolve these problems.

According to the present invention there is provided a more economical and more effective process for splitting primary and secondary alkylaromatic hydroperoxides which comprises reacting the hydroperoxide with a catalytic amount of an acid reaction in the presence of an inert organic solvent, this solvent being an aprotic polar solvent which is a polymethylene-sulphone or an alkylene glycol carbonate which contains 2 to 4 carbon atoms (in the alkylene portion).

The alkylaromatic hydroperoxides which may be used generally have the formula:

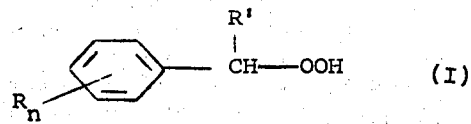

(I)

in which:

R, which can be situated in the ortho-, meta- or para-position relative to the hydrocarbon chain of the aromatic nucleus carrying the hydroperoxide group, represents: a hydrogen atom; an alkyl radical containing 1 to 4 carbon atoms, for example a methyl, ethyl, n-propyl, isopropyl, n-butyl or isobutyl radical, optionally substituted by a halogen atom such as chlorine, bromine or fluorine, or by a nitro group or by an alkoxy group containing 1 to 4 carbon atoms; a halogen atom; a nitro group; or an alkoxy radical such as defined above;

R' represents; a hydrogen atom; an alkyl radical containing 1 to 4 carbon atoms such as defined above; a cycloalkyl radical such as the cyclohexyl radical; an aryl radical such as the phenyl radical; or an aralkyl radical such as the benzyl radical; or, together with R, if R is in the ortho-position, forms a single divalent alkylene radical such as the trimethylene radical; and $n$ represents an integer from 1 to 3.

Specific examples of alkylaromatic hydroperoxides which can be used in the process of the present invention include: benzyl hydroperoxide, o-xylyl hydroperoxide, p-xylyl hydroperoxide, p-ethylbenzyl hydroperoxide, p-isopropylbenzyl hydroperoxide, 2,4-dimethylbenzyl hydroperoxide, 3,5-dimethyl-benzyl hydroperoxide, 2,4,6-trimethyl-benzyl hydroperoxide, p-methoxybenzyl hydroperoxide, 1-phenyl-ethyl hydroperoxide, 1-(p-methylphenyl)-ethyl hydroperoxide, 1-(o-ethylphenyl)-ethyl hydroperoxide, 1-(p-ethylphenyl)-ethyl hydroperoxide, 1-(2,4-dimethyl-phenyl)-phenyl)-ethyl hydroperoxide, 1-(3,5-dimethylphenyl)-ethyl hydroperoxide, 1-(p-chlorophenyl)-ethyl hydroperoxide, 1-(p-methoxyphenyl)-ethyl hydroperoxide, 1-(p-nitrophenyl)-ethyl hydroperoxide, 1-phenyl-n-propyl hydroperoxide, 1-phenyl-n-butyl hydroperoxide, 1-phenyl-2,2-dimethyl-n-propyl hydroperoxide, cyclohexyl-phenylmethyl hydroperoxide, diphenylmethyl hydroperoxide, (o-methylphenyl)-phenylmethyl hydroperoxide, (p-methylphenyl)-phenylmethyl hydroperoxide, (p-chlorophenyl)-phenylmethyl hydroperoxide, (p-methoxyphenyl)-phenylmethyl hydroperoxide, 1,2-diphenyl-ethyl hydroperoxide and α-tetralyl hydroperoxide.

The splitting process according to this invention is particularly suitable for hydroperoxides of the formula (I) in which R represents a hydrogen atom or a methyl radical, the aromatic nucleus being preferably monosubstituted, and R' represents a hydrogen atom or a hydrocarbon radical such as a methyl or benzyl radical, for example benzyl hydroperoxide, p-xylyl hydroperoxide, 1-phenyl-ethyl hydroperoxide and 1,2-diphenyl-ethyl hydroperoxide.

The primary and secondary hydroperoxides used in the process of the present invention are known and can be prepared by the usual methods by passing a gas containing oxygen, under non-catalytic conditions, in the liquid phase, through the corresponding hydrocarbon heated to the desired temperature; the hydroperoxides obtained are purified in accordance with conventional methods, such as conversion to the sodium salt and treatment with carbon dioxide.

As polymethylene-sulphones which may be used those which contain 3 to 6 methylene groups, it being possible for one or more of these methylene groups optionally to be substituted by alkyl radicals with 1 to 4 carbon atoms (for example methyl, ethyl, propyl and butyl radicals), are preferred.

Specific examples of such sulphones include trimethylene-sulphone, α-methyltrimethylene-sulphone, α-methyltetramethylene-sulphone, tetramethylene-sulphone (sulpholane), pentamethylene-sulphone, α-methylpentamethylenesulphone, hexamethylene-sulphone and α,α'-dimethyltetramethylene-sulphone. Preferred polymethylene-sulphones are sulpholane, which is especially preferred, and its alkyl-substituted derivatives, such as those described in French Pat. No. 1,342,449.

Suitable glycol carbonates include ethylene glycol carbonate, propylene glycol carbonate and butane-2,3-diol carbonate.

The abovementioned polar solvents make it possible to effect the splitting of the primary and secondary alkyl aromatic hydroperoxides, in the presence of catalytic amounts an acid, the selectivity towards phenolic products is at least equal to and is generally greater than that which pertains in the prior art processes. Moreover, and this is a particular advantage, the reaction times necessary to obtain high conversion rates are very markedly shorter; thus they can be of the order of a few minutes.

In practice, one method of carrying out the process consists of introducing the hydroperoxide in the pure state into a mixture consisting of the compound with an acid reaction in the chosen polar solvent, heated beforehand to from 20°C to the reflux temperature of the mixture, preferably from 50°C to 110°C; the hydroperoxide can also be introduced into this mixture in the form of a solution in the chosen polar solvent.

It is however not necessary to use a rigorously pure hydroperoxide; it is possible to use a crude product resulting from the partial oxidation of the hydrocarbon, after having freed the crude product from the greater part of the excess unconverted hydrocarbon, for example by distillation.

The acidic agent used is suitably an inorganic or organic protonic acid, such as those used heretofore. Particularly suitably acids include hydrochloric acid, nitric acid, sulphuric acid, alkanesulphonic acids such as methanesulphonic acid, and arylsulphonic acids such as benzenesulphonic and para-toluenesulphonic acids. The acid is preferably used in the form of the pure acid or of a concentrated aqueous solution. Although protonic acids are preferred, it is also possible to use acid catalysts such as anhydrous ferric chloride, boron trichloride, silica, diatomaceous earth, and Friedel-Crafts catalysts such as aluminium chloride and zinc chloride.

The amount of pure acid agent employed to split the hydroperoxides can vary within quite wide limits; it has been found that amounts from 0.1% to 10% by weight based on the hydroperoxide employed are generally sufficient to effect the splitting reaction rapidly.

The concentration of the hydroperoxide in the selected polar solvent is not critical.

When the introduction of the hydroperoxide is complete, the reaction is allowed to continue, at the desired temperature, for the period of time necessary to achieve as complete a conversion of the hydroperoxide as possible, with the minimum amount of degradation reactions. The reaction mixture can then, where appropriate, be neutralised by a base.

When a protonic acid is used, the small amount which is necessary is completely soluble in the medium, so that the reaction mixture is perfectly homogeneous and only moderate stirring is required in order to bring the reagents into contact. Furthermore, when the reaction mixture is neutralised, the amount of basic agent necessary can be very low, as a consequence only small amounts of the corresponding salts are formed, which are partially dissolved in the medium, so that it is possible to dispense with an additional separation step.

The residual solution can be treated in a suitable manner to isolate the desired phenolic and carbonyl products therefrom, for example by fractional distillation. If so desired, it is possible to work under temperature and pressure conditions such that the carbonyl derivative is removed as it is formed.

The following Examples further illustrate the present invention.

EXAMPLE 1

12.5 G of sulpholane containing 0.05 g of 98% by weight sulphuric acid are introduced into a glass flask which is equipped with a central stirring system, a reflux condenser, a dropping funnel and a thermometer and an external heater, the mixture is heated to 100°C and 1.82g of benzyl hydroperoxide containing 85% by weight of pure hydroperoxide are then added rapidly.

When the addition is complete, the reaction mixture is stirred at the selected temperature for a definite period of time, until complete deperoxidation has taken place. Heating is then stopped and the strong acid is neutralised by means of the theoretical amount of a normal solution of sodium hydroxide in methanol.

The yields of phenol and benzaldehyde, relative to the pure hydroperoxide employed, are measured by vapour phase chromatographic analysis.

The same experiment was repeated, using methylcyclohexane instead of sulpholane (experiment A).

The following table give the results obtained:

| Example/Experiment | 1 | Experiment A |
|---|---|---|
| Solvent, grams | Sulpholane 12.5 | Methylcyclohexane |

-continued

| Example/Experiment | 1 | Experiment A |
|---|---|---|
| Pure benzyl hydroperoxide, mols | 0.0125 | 12.5 0.0125 |
| Pure H$_2$SO$_4$, mols | 0.0005 | 0.0005 |
| Molar ratio: $\frac{H_2SO_4}{hydroperoxide}$ | 0.04 | 0.04 |
| % $\frac{H_2SO_4}{hydroperoxide}$ by wt. | 3.16% | 3.16% |
| Temperature, °C | 100° | 100° |
| Duration | 7 minutes | 1 hour 10 minutes |
| % residual peroxide oxygen | 0% | 0% |
| Yield ⟨phenyl⟩—OH | 38.9% | 18.3% |
| Yield ⟨phenyl⟩—CHO | 30.8% | 30% |

Preparation of Benzyl Hydroperoxide

750 G of toluene are introduced into a 1.5 liter stainless steel autoclave which is shaken; the toluene is oxidised, at 180°C under a pressure of 20 bars, with air depleted of oxygen until it contains only 8%, with an hourly flow rate of 240 liters (measured under normal temperature and pressure). After 1 hour 30 minutes the reaction mixture is cooled. The hydroperoxide is then purified via its sodium salt. 11.4 G of benzyl hydroperoxide, containing 85% by weight of pure product, are thus obtained.

EXAMPLE 2

12.5 G of sulpholane containing 0.05 g of 98% by weight sulphuric acid are introduced into a glass flask which is equipped as in Example 1 and is heated externally; the mixture is heated to 60°C and 2.77 g of p-xylyl hydroperoxide containing 62.5% by weight of pure hydroperoxide are then added rapidly.

Once the addition is complete, the reaction mixture is stirred at the selected temperature for a definite period of time, until deperoxidation ceases. The procedure of Example 1 is then followed.

The yields of p-cresol and p-tolualdehyde, relative to the pure hydroperoxide employed, are measured by vapour phase chromatographic analysis.

The following table gives the results obtained:

| Example | 2 |
|---|---|
| Sulpholane, grams | 12.5 |
| Pure p-xylyl hydroperoxide, mols | 0.0125 |
| Pure H$_2$SO$_4$, mols | 0.0005 |
| Molar ratio: $\frac{H_2SO_4}{hydroperoxide}$ | 0.04 |
| % $\frac{H_2SO_4}{hydroperoxide}$ by wt. | 2.83% |
| Temperature, °C | 60° |
| Duration | 7 minutes |
| % Peroxide oxygen | 16.8% |
| Yield CH$_3$—⟨phenyl⟩—OH | 51% |
| Yield CH$_3$—⟨phenyl⟩—CHO | 17.4% |

Preparation of P-xylyl Hydroperoxide

It is prepared by oxidising p-xylene (750 g) in a 1.5 liter stainless steel autoclave, by means of air depleted in oxygen (air containing 8% of oxygen, flow rate of 240 liters per hour calculated under normal temperature and pressure), at 175°C under a pressure of 20 bars. After 50 minutes, the mixture is cooled and is then transferred to a one liter boiler. The unconverted p-xylene is then removed by distillation under reduced pressure, without exceeding 40°C in the boiler. 57.4 g of oxidised products, containing 62.5% by weight of p-xylyl hydroperoxide, are thus obtained.

EXAMPLES 3 AND 4

25.4 G of sulpholane (Example 3) containing 0.1 g of 98% by weight sulphuric acid are introduced into a glass flask which is equipped as in Example 1 and is heated externally; the mixture is heated to 100°C and 3.57g of 1-phenyl-ethyl hydroperoxide containing 96.7% by weight of pure hydroperoxide are then added rapidly.

Once the addition is complete, the reaction mixture is stirred at the chosen temperature for a definite period of time, until complete deperoxidation has taken place. The procedure of Example 1 is followed thereafter.

The process is repeated using 25 g of ethylene glycol carbonate as the reaction solvent (Example 4).

By way of comparison, these experiments were repeated using either non-polar solvents such as ethylbenzene (Experiment B), or basic solvents such as dioxane (Experiment C) and acetonitrile (Experiment D).

The yields of phenol and carbonyl products formed, relative to the pure hydroperoxide employed, are measured by vapour phase chromatographic analysis.

The following table gives the results obtained:

| EXAMPLE/EXPERIMENT | 3 | 4 | EXPERIMENT B | EXPERIMINT C | EXPERIMENT D |
|---|---|---|---|---|---|
| Solvent, grams | Sulpholane 25.4 | Ethylene glycol carbonate 25 | Ethylbenzene 17.4 | Dioxane 20.6 | Acetonitrile 15.66 |
| Pure 1-phenyl-ethyl hydroperoxide, mols | 0.025 | 0.025 | 0.025 | 0.025 | 0.025 |
| Pure H$_2$SO$_4$, mols | 0.001 | 0.001 | 0.001 | 0.001 | 0.001 |
| Molar ratio: H$_2$SO$_4$/hydroperoxide H$_2$SO$_4$ | 0.04 | 0.04 | 0.04 | 0.04 | 0.04 |

-continued

| EXAMPLE/EXPERIMENT | 3 | 4 | EXPERIMENT B | EXPERIMINT C | EXPERIMENT D |
|---|---|---|---|---|---|
| % hydroperoxide by wt. | 2.84% | 2.84% | 2.84% | 2.84% | 2.84% |
| Temperature, °C | 100° | 100° | 100° | 100° | 80° |
| Duration | 5 minutes | 3 minutes | 5 minutes | 6 hours | 1 hour |
| % Residual peroxide oxygen | 0% | 0% | 0% | 0% | 0% |
| Yields Ph-OH | 85.7% | 90% | 40% | 30% | 50.6% |
| Yields of carbonyl products (%) | $CH_3CHO$ 77% | | Ph-$COCH_3$ 14.8% | Ph-$COCH_3$ 35% | Ph-$COCH_3$ 12.6% |
| | Ph-$COCH_3$ 2.6% | | Ph-CHO 17.6% | Ph-CHO 10% | Ph-CHO 15% |
| | Ph-CHO 0.5% | | | | |

PREPARATION OF 1-PHENYL-ETHYL HYDROPEROXIDE

It is prepared by oxidising ethylbenzene in a manner similar to that described for the oxidation of toluene (Example 1) of p-xylene (Example 2), but the reaction is carried out at 130°C under a pressure of 6 bars. After 5 hours oxidised products containing 11% by weight of 1-phenylethyl hydroperoxide are obtained. The hydroperoxide is purified by extraction with an aqueous solution of sodium hydroxide, and a product containing 96.7% by weight of pure 1-phenyl-ethyl hydroperoxide is isolated.

EXAMPLE 5

12.5 G of sulpholane containing 0.05 g of 98% by weight sulphuric acid are introduced into a glass flask which is equipped as in Example 1 and is heated externally; the mixture is heated to 80°C and 2.98 g of 1,2-diphenyl-ethyl hydroperoxide containing 90% by weight of pure hydroperoxide are then added rapidly. Once the addition is complete, the mixture is stirred at the chosen temperature for a definite period of time, until deperoxidation ceases. The procedure of Example 1 is followed thereafter.

The yields of phenol and carbonyl products formed, relative to the pure hydroperoxide employed, are measured by vapour phase chromatographic analysis.

An experiment starting with 28 g of benzene, 5.39 g of 1,2-diphenyl-ethyl hydroperoxide containing 91% by weight of pure hydroperoxide, and 0.54 g of 98% by weight sulphuric acid (Experiment E) was also carried out. The carbonyl products formed are measured by converting them to oximes.

The following table gives the results obtained:

| Example/Experiment | 5 | Experiment E |
|---|---|---|
| Solvent, grams | Sulpholane 12.5 | Benzene 28 |
| Pure 1,2-diphenyl-ethyl-hydroperoxide, mol | 0.0125 | 0.0229 |
| Pure $H_2SO_4$, mols | 0.0005 | 0.0054 |
| Molar ratio: $H_2SO_4$/hydroperoxide | 0.04 | 0.24 |
| % $H_2SO_4$/hydroperoxide, by weight | 1.83% | 10.79% |
| Temperature, °C | 80° | 40° |
| Duration | 2 minutes 30 seconds | 1 hour 30 minutes |
| % Residual peroxide oxygen | 4% | 0% |
| Yield Ph-OH | 72% | — |
| Yield of carbonyl products Ph-$CH_2CHO$ | 59% | Less than 20% |
| Ph-CHO | 17.5 % | |

PREPARATION OF 1,2-DIPHENYL-ETHYL HYDROPEROXIDE

200 G of recrystallised dibenzyl are introduced into a glass flask and are heated to 135°C whilst a flow rate of air of 60 liters per hour (measured under normal temperature and pressure) is established. After 3 hours 15 minutes, the oxidised products contain 18 g of 1,2-diphenyl-ethyl hydroperoxide. The hydroperoxide is purified thereafter via its sodium salt. 13.3 G of 1,2-diphenyl-ethyl hydroperoxide containing 90% by weight of pure product are thus isolated.

We claim:

1. In a process for converting a primary or secondary alkylaromatic hydroperoxide of the general formula:

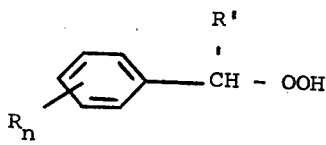

in which:

R represents a hydrogen or halogen atom, an alkyl radical containing 1 to 4 carbon atoms, a said alkyl radical substituted by a halogen atom, a nitro or alkoxy radical containing 1 to 4 carbon atoms, a nitro group, or an alkoxy radical containing 1 to 4 carbon atoms;

R' represents a hydrogen atom; an alkyl radical containing 1 to 4 carbon atoms; a cycloalkyl radical; an aryl radical; or an aralkyl radical or, when R is in the ortho-position, together with R forms a divalent alkylene radical; and n represents an integer from 1 to 3, into phenolic and/or carbonyl compounds, which comprises reacting the hydroperoxide with a catalytic amount of a acid catalyst in the presence of an inert organic solvent, the improvement wherein the solvent is an aprotic polar solvent selected from a polymethylene-sulphone containing 3 to 6 methylene groups, one or more of said methylene groups optionally being substituted by an alkyl radical with 1 to 4 carbon atoms, and alkylene glycol carbonate containing 2 to 4 carbon atoms in the alkylene part.

2. A process according to claim 1, in which R' represents a cyclohexyl, phenyl or benzyl radical.

3. Process according to claim 1, in which the hydroperoxide is benzyl hydroperoxide, p-xylyl hydroperoxide, 1-phenyl-ethyl hydroperoxide or 1,2-diphenyl-ethyl hydroperoxide.

4. Process according to claim 1, in which the solvent is sulpholane, ethylene glycol carbonate or propylene glycol carbonate.

5. Process according to claim 1 in which the acid catalyst is an inorganic protonic acid or organosulphonic acid.

6. Process according to claim 5, in which the protonic acid is selected from hydrochloric acid, nitric acid, sulphuric acid, methanesulphonic acid, benzenesulphonic acid and para-toluenesulphonic acid.

7. Process according to claim 6, in which the protonic acid is present as pure acid or as a concentrated aqueous solution.

8. Process according to claim 1, which is carried out in the liquid phase, at a temperature of from 20°C to the boiling point of the reaction mixture.

9. Process according to claim 8, which is carried out at 50° to 110°C.

10. Process according to claim 1, in which the acid catalyst is present in an amount from 0.1% to 10% by weight (expressed as pure acid), based on the weight of the hydroperoxide.

11. Process according to claim 1, which is carried out at 50° to 110°C in the presence of sulpholane, ethylene glycol or propylene glycol carbonate and a protonic acid selected from hydrochloric acid, nitric acid, sulphuric acid, methanesulphonic acid, benzenesulphonic acid and para-toluene sulphonic acid.

* * * * *

UNITED STATES PATENT OFFICE
CERTIFICATE OF CORRECTION

Patent No. 3,948,995      Dated April 6, 1976

Inventor(s) Michel Jouffret

It is certified that error appears in the above-identified patent and that said Letters Patent are hereby corrected as shown below:

In the heading:

Change the name of the assignee from "Rhone-Poulenc Textile" to --Rhone-Poulenc S. A.--

Signed and Sealed this

Fourth Day of January 1977

[SEAL]

Attest:

RUTH C. MASON
Attesting Officer

C. MARSHALL DANN
Commissioner of Patents and Trademarks